United States Patent [19]

Birring et al.

[11] Patent Number: 4,890,496

[45] Date of Patent: Jan. 2, 1990

[54] METHOD AND MEANS FOR DETECTION OF HYDROGEN ATTACK BY ULTRASONIC WAVE VELOCITY MEASUREMENTS

[75] Inventors: Anmol S. Birring; David G. Alcazar; Gary J. Hendrix; John J. Hanley, all of San Antonio, Tex.

[73] Assignee: Electric Power Research Institute, Palo Alto, Calif.

[21] Appl. No.: 241,504

[22] Filed: Sep. 7, 1988

[51] Int. Cl.⁴ .......................................... G01N 29/04
[52] U.S. Cl. ........................................ 73/597; 73/599
[58] Field of Search ................. 73/597, 599, 622, 637, 73/640

[56] References Cited

U.S. PATENT DOCUMENTS

| | | | |
|---|---|---|---|
| 3,416,365 | 12/1968 | Frederick | 73/597 |
| 4,386,527 | 6/1983 | Maucher | 73/597 |
| 4,685,334 | 8/1987 | Latimer | 73/622 |

OTHER PUBLICATIONS

Szilard, J., "Ultrasonic Testing" pp. 612–621 (1982).
Singh, "Inspection for Hydrogen Damage in Boiler Water Wall Tubes" Materials Eval. (1985), Sep.
Watanabe et al, "Ultrasonic Velocity Ratio Method for Detecting and Evaluating Hydrogen Attack in Steels" ASTM, pp. 153–165, May 22–24 (1984).
Failures & Inspection of Fossil–Fired Boiler Tubes: 1983 Conference & Workshop, CS-3272, Contract WS 82-101, Dec. 1983, Articles: a. "Inspection for Hydrogen Damage in Waterwall Tubes Using Ultrasonic Techniques", Sloat et al., b. "Mitigating Forced Outages by Selective Replacement of Boiler Tubes" Loper et al., c. "Working Group on Hydrogen Damage, Pitting and Deposits", Freeh et al.

Primary Examiner—John Chapman
Assistant Examiner—Lawrence Fess
Attorney, Agent, or Firm—Flehr, Hohbach, Test, Albritton & Herbert

[57] ABSTRACT

A method for detecting hydrogen attack by ultrasound wave velocity measurements in which ultrasound waves (e.g. longitudinal, shear, or creeping) are transmitted from one transducer to another transducer along a fixed path through a steel body such as pipe. The velocity of the ultrasound wave is determined with an accuracy of 0.1 percent from the fixed path length and the time for a wave to travel from one transducer to the other transducer. A decrease in velocity by more than two percent indicates hydrogen attack. In one embodiment, either refracted longitudinal or refracted shear waves are transmitted, and the velocities thereof are determined. In another embodiment, a creeping wave is transmitted from one transducer to the other transducer with the creeping wave including a surface wave and a subsurface wave. Travel time of the subsurface wave is measured and used with the known fixed path length in determining velocity. In the third embodiment ultrasonic waves are transmitted into the material and the backscattered ultrasound is measured. An increase in backscattered ultrasound is related to hydrogen attack.

9 Claims, 4 Drawing Sheets

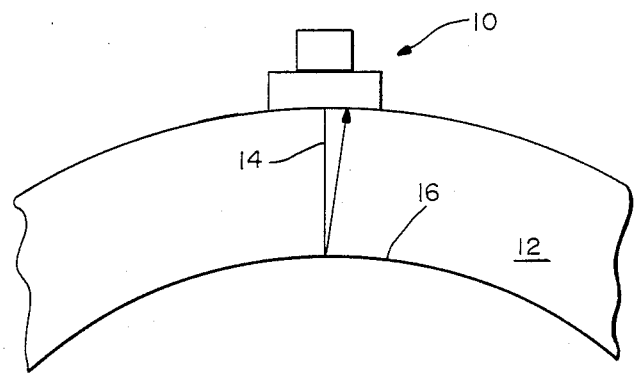
(PRIOR ART)
FIG.—1A
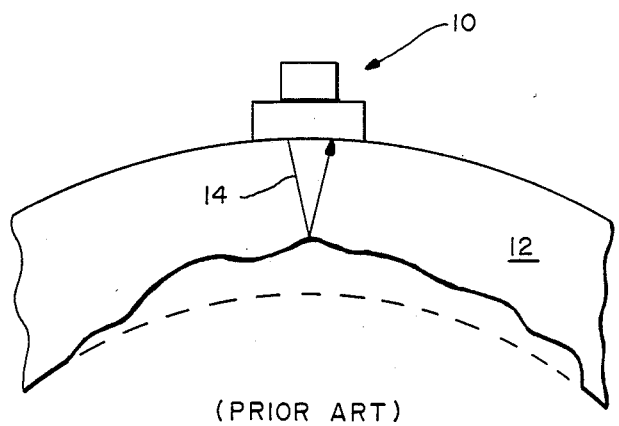
(PRIOR ART)
FIG.—1B
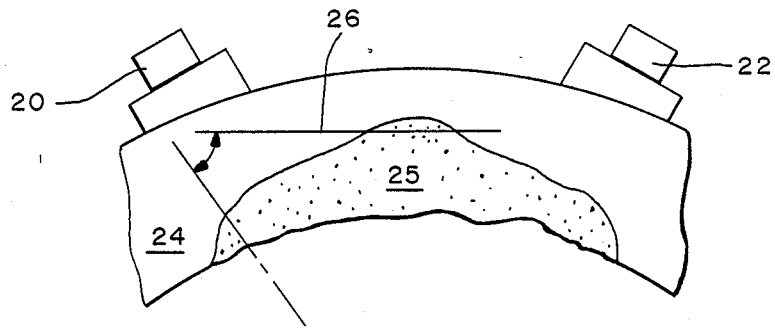
FIG.—2

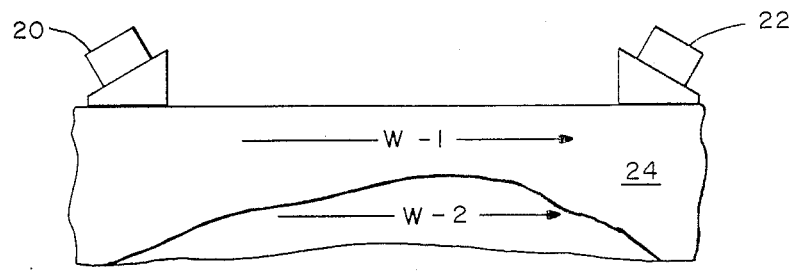
FIG.—3
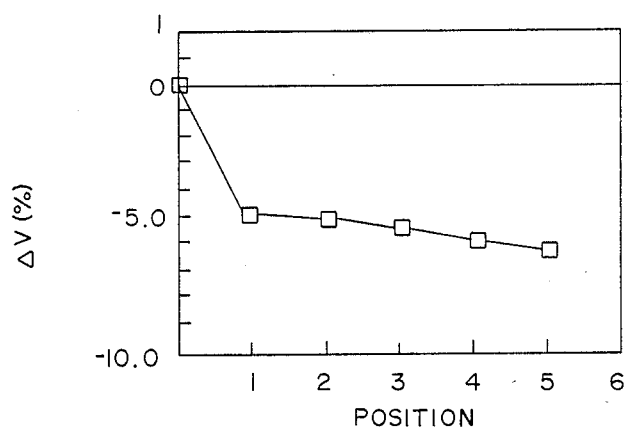
FIG.—4A
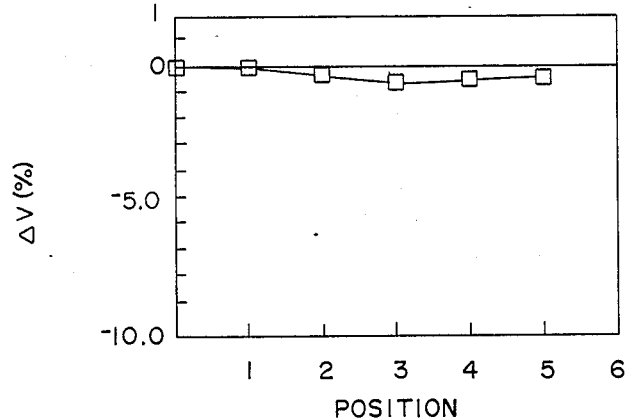
FIG.—4B

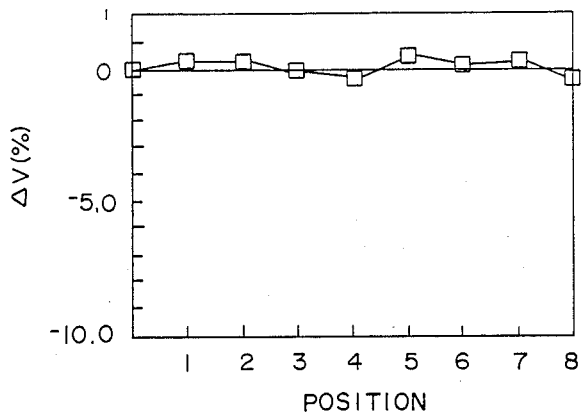
FIG.—4C
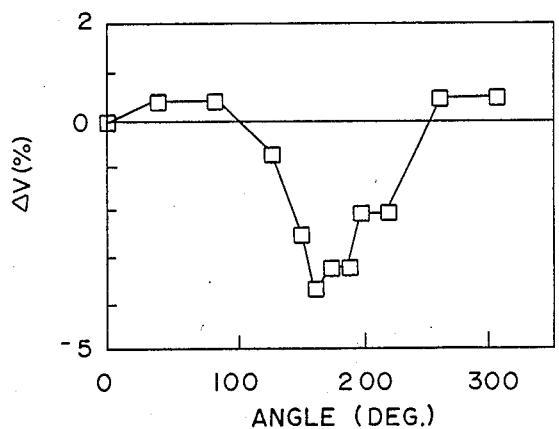
FIG.—5A
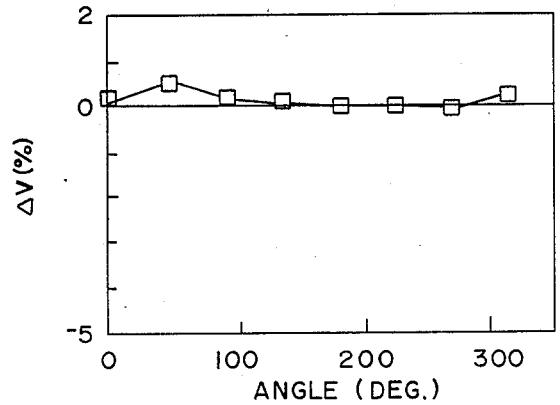
FIG.—5B

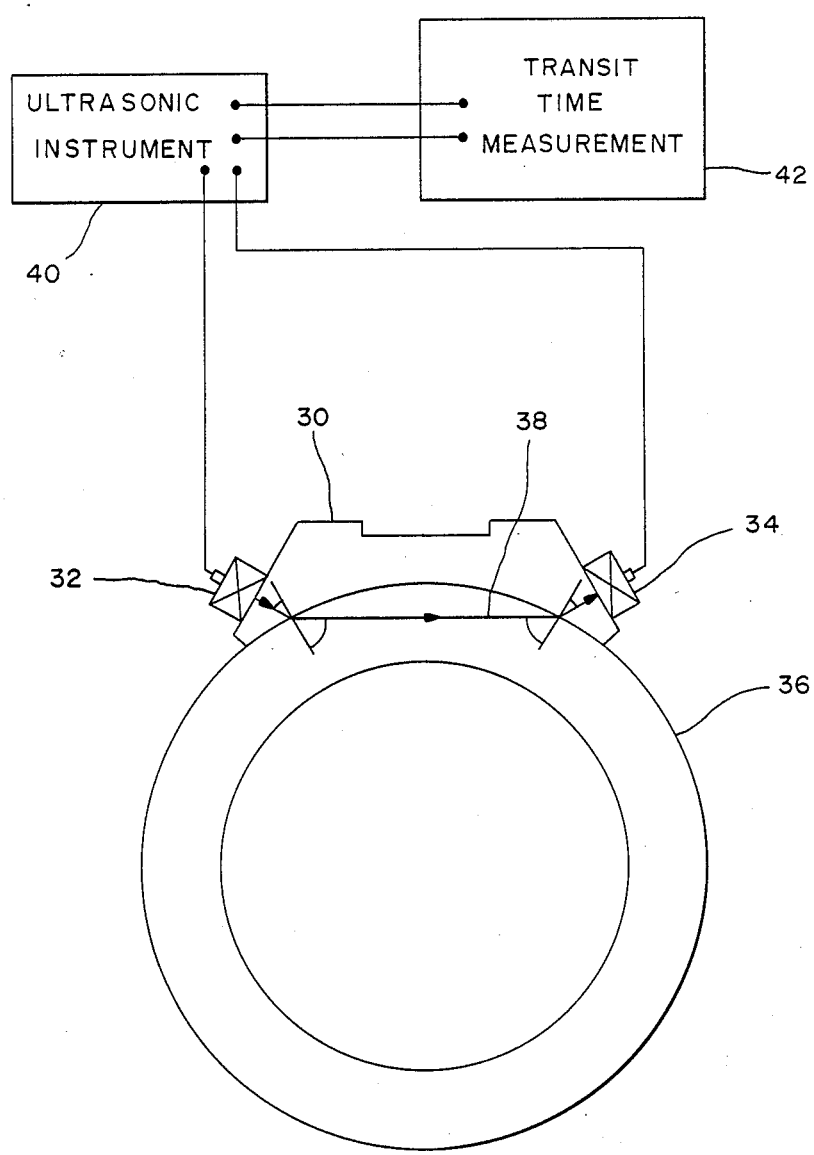
FIG.—6
FIG.—7

METHOD AND MEANS FOR DETECTION OF HYDROGEN ATTACK BY ULTRASONIC WAVE VELOCITY MEASUREMENTS

BACKGROUND OF THE INVENTION

This invention relates generally to nondestructive testing for structural defects, and more particularly the invention relates to the detection of hydrogen attack in steel products such as pipe through ultrasonic testing techniques.

Hydrogen damage or attack is produced in steels by a hydrogen reaction with carbides which forms methane gas and decarburizes the steel. This process lowers the fracture toughness of steel without necessarily reducing wall thickness. Detection of hydrogen attack is important to assure safe operation of boiler tubes, pressure vessels, and piping subject to such damage.

More particularly, hydrogen damage or attack is produced in steels exposed to a high-pressure hydrogen environment at high temperatures. Under such conditions, a chemical reaction occurs between hydrogen and carbides in steel to produce methane gas bubbles in the grain boundaries. As the bubbles grow, they interlink to form intergranular fissures or microcracks. The kinetics of hydrogen attack depend on several variables including the temperature, pressure, and fluid being contained. In general, the chemical reaction for hydrogen attack can be simplified to:

$$Fe_3C + 2H_2 \rightarrow CH_4 + 3Fe \tag{1}$$

In petrochemical plants, hydrogen for equation (1) is present in the fluid stream in a tube or pipe. In the case of boiler tubes in fossil plants, hydrogen can be generated by a corrosion reaction of iron with water:

$$3Fe + 4H_2O \rightarrow Fe_3O_4 + 4H_2 \tag{2}$$

The hydrogen available from the reaction in equation (2) is then used to promote the reaction in equation (1). Because the reaction of equation 2 is on the inside surface face (ID), hydrogen damage in boiler tubes is usually associated with corrosion and pitting at the inside diameter. As the hydrogen interacts with the steel to form methane gas, the gas bubbles at the grain boundaries and the decarburization of the steel reduce the material's fracture toughness. This loss of structural integrity from hydrogen attack has been known to produce several failures in fossil fuel and petrochemical plants.

Heretofore, ultrasonic techniques have been employed to detect structural defects such as large isolated cracks and wall thinning due to corrosion. The total transit time of an ultrasonic wave transmitted to and reflected from the defect or inner wall is used to determine distances in locating flaws or the thickness of the wall. Such transit-time measurements are typically made in microseconds.

Theoretical and laboratory studies have indicated that microcracks caused by hydrogen attack will affect both attenuation and velocity of an acoustic wave in a steel body. However, use of conventional ultrasonic testing techniques to identify the location and magnitude of such microcracks has resulted in inconsistent results in the field applications.

SUMMARY OF THE INVENTION

An object of the invention is an improved method of detecting hydrogen attack in steel pipes and the like.

Another object of the invention is apparatus useful in field applications for detecting hydrogen attack in steel pipe and other steel material.

A feature of the invention is the measurement of velocity of ultrasonic waves travelling through a steel pipe along one or more paths.

Briefly, transit time changes of an ultrasonic wave caused by hydrogen attack are measured. Such transit time changes are of the order of 50–500 nanoseconds in steam boiler tubes where velocity changes by two to ten percent due to hydrogen attack. Advantageously, due to transducer configurations, the transit time is not affected by corrosion or the inside of the boiler tube.

In a preferred embodiment, a special transducer shoe is utilized to maintain a fixed distance for travel of ultrasonic waves in a product undergoing test in field applications.

The invention and objects and features thereof will be more readily apparent from the following detailed description and appended claims when taken with the drawing.

BRIEF DESCRIPTION OF THE DRAWING

FIG. 1A and FIG. 1B illustrate prior-art nondestructive testing of a steel pipe for cracks and wall thinning due to corrosion, respectively.

FIG. 2 illustrates the application of ultrasonic longitudinal or shear waves in accordance with the present invention in determining the presence of hydrogen attack in a steel pipe.

FIG. 3 illustrates the application of near-surface ultrasonic creeping waves in determining the presence of hydrogen attack in accordance with another embodiment of the invention.

FIGS. 4A–4C are graphs illustrating the results of refracted shear wave velocity measurements using the embodiment of FIG. 2.

FIGS. 5A and 5B are graphs illustrating the results of creeping wave velocity measurements taken at various angular locations along a tube circumference using the technique of FIG. 4.

FIG. 6 illustrates the application of ultrasonic backscatter in determining the presence of hydrogen attack in a tube not experiencing corrosion.

FIG. 7 is a block diagram of a field test system including a shoe for holding transducers for field use in carrying out the invention.

DETAILED DESCRIPTION OF ILLUSTRATIVE EMBODIMENTS

FIGS. 1A and 1B illustrate non-destructive testing techniques utilizing ultrasonic waves in measuring attenuation or velocity and wall thinning due to corrosion, respectively.

In FIG. 1A, a transducer 10 is placed on the outer surface of a pipe 12 and an ultrasonic wave 14 is transmitted into the wall of the pipe. The inner surface of the tube 12 reflects the ultrasonic wave 14 which is then received by the transducer 10. Measurement of the total time from wave transmission to reflected wave reception and the tube thickness gives a measure of the velocity. A decrease of reflected signal amplitude for the ultrasonic wave 14 is a measure of attenuation.

Similarly, in FIG. 1B, the transducer 10 is again placed on the outer surface of a pipe 12 whose inner wall has been corroded. The transducer again transmits the ultrasonic wave 14 which is reflected by the inner surface of pipe 12 and then received by the transducer 10. The total travel time of the ultrasonic wave 14 gives a measure of the thickness of the wall of pipe 12 and thus an indication of thinning of the pipe wall due to corrosion.

In the prior-art techniques illustrated in FIGS. 1A and 1B, the time measurements are relatively large, on the order of microseconds. Such a technique is satisfactory in detecting large isolated flaws or measuring thickness of material. However, the configuration is not satisfactory for measuring velocity changes with an accuracy of 0.1%. Velocity which is equal to twice the thickness divided by the transit time in FIG. 1A cannot be calculated as the thickness of tube is unknown to the required accuracy. The attenuation method that measures the loss of reflected signal amplitude is not satisfactory as the signal amplitude is influenced by other variables such as corrosion, surface roughness and coupling. These variables produce inconsistent results in attenuation measurements and in determining the presence of hydrogen attack in a steel tube.

In accordance with the present invention, the identification of microcracks indicative of hydrogen attack on a steel pipe or similar steel body is attained by velocity measurements that are performed with an accuracy of 0.1%. More particularly, transducers are arranged on the surface of a pipe so that a fixed path length is maintained. Acoustic waves, longitudinal, shear, or creeping, are utilized in the velocity measurements. By measuring the transit time changes of ultrasound waves through different paths in the pipe, changes in ultrasonic wave velocity in the paths are determined. Such transit time changes are of the order of 50 to 500 nanoseconds in boiler tubes when velocity changes are two to ten percent. Importantly, the transducers can be arranged so that the transit time is unaffected by corrosion on the inside of a boiler tube. Further, the transducer configuration does not require knowledge of tube thickness to measure changes in velocity.

Referring now to FIG. 2, one embodiment of the invention is illustrated in which the transducers 20 and 22 are placed on the outer surface of a tube 24 suffering from hydrogen attack and corrosion as illustrated at 25. In this embodiment, either longitudinal or shear waves are transmitted from transducer 20 to transducer 22 and the changes in velocity are measured along different paths. In the path 26, the velocity is decreased due to the path traversing into the hydrogen attack region of the pipe.

FIG. 3 illustrates another embodiment of the invention in which the transducers 20, 22 are positioned on the outer surface of a pipe 24 in axial displacement. In this embodiment, near-surface or "creeping" ultrasonic waves are transmitted. In this configuration, one wave, $W_1$, travels at or near the surface, whereas a second wave, $W_2$, penetrates deeper into the pipe thickness and its velocity is affected by the scattering from the microcracks produced by hydrogen attack, as shown. The transit time of the second pulse, $W_2$, is therefore measured for detection of hydrogen attack.

Experimental tests were performed on a set of samples, called Set B. Set B was taken from boiler tubes of a fossil-fired power plant and consisted of 19 boiler-tube samples with lengths varying from 5 to 7.5 cm (2 to 3 inches), an outer diameter of 7.5 cm (3 inches), and a thickness of 0.8 cm (0.32 inch). Samples B-1 through B-10 had hydrogen attack while the remainder had no attack. Sample B-19 contained machined pits with a depth up to 50 percent of the thickness. Samples B-1 through B-18 were taken from one utility while B-19 was taken from another. Hydrogen attack in the set of tubes was always associated with heavy corrosion. Hydrogen attack was verified in the tubes by etching with 50-percent hydrochloric acid at 80° C. for 5 minutes.

Velocity measurements in boilers tubes are difficult to take at normal incidence because ultrasonic scattering at the ID surface inhibits resolution of backsurface reflection from the noise. Ultrasonic velocity measurements, however, can be taken in different configurations, such as shown in FIGS. 2 and 3.

The configuration of FIG. 2 transmits refracted L-waves or S-waves in the chordal direction with the centerline of the beam being tangential to the mid-thickness. In this configuration, the transit time of the earliest arrival signal was measured. The configuration of FIG. 3 used the time measurement of creeping or near-surface waves. The creeping wave was produced by 90-degree refracted L-waves. In this configuration, the transit time was measured for the second signal (W-2). This was done because the creeping wave is believed to have two roughly equal components. The arrival of the earliest pulse (W-1) corresponds to the wave that travels at the surface. The transit time of the earliest pulse is not affected by hydrogen attack because the damage is not present at the OD. The second pulse (W-2) penetrates deeper in the tube thickness, and its velocity is affected by scattering from the microcracks produced by hydrogen attack. The transit time of the second pulse (W-2) was therefore measured for detection of hydrogen attack.

Representative results of the ultrasonic velocity of time measurement are presented in FIGS. 4A–4C and FIGS. 5A and 5B. FIGS. 4A–4C present the results of the 75-degree refracted L-waves for the configuration in FIG. 2. Representative plots of the ultrasonic velocity at locations along the length of the tube are shown. Ultrasonic velocities in the hydrogen-attacked regions dropped by 6.5 percent for refracted L-waves in FIG. 4A. Velocity of refracted longitudinal waves dropped up to 9.3% in damaged tubes and were found more sensitive than shear waves. A drop of less than 1.0% was observed on tubes with no damage. Representative results on the creeping waves are shown in FIGS. 5A and 5B. Creeping-wave velocity dropped by as such as 3.7 percent on a tube with hydrogen attack (FIG. 5A).

The results of the velocity measurements, shown in Table 1, clearly demonstrate that the ultrasonic velocities were reduced by the presence of hydrogen attack. Depending upon configuration, reduction could be up to 9.3% in the tubes. The velocity variation in the samples with no damage was always less than 1.0%. Moreover, no significant velocity reduction was found on samples with ID pitting (B-12 and B-18) or sample B-19 with machined pits, clearly demonstrating that velocity reduction in boiler tubes was caused by hydrogen attack and not by pitting or corrosion. Sample B-1 did not show any velocity reduction, as the depth of damage was minimal and localized towards one end of the tube. Moreover, the depth of the actual damage in Table 1 represents the etching results on only one end of the tube. The variation of damage at other locations in the tube is unknown.

TABLE 1

ULTRASONIC VELOCITY (MM/μSEC) RESULTS FROM BOILER-TUBE SAMPLES. CHANGES IN VELOCITY (ΔV %) ARE COMPUTED RELATIVE TO NOMINAL VALUE OF 5.94 MM/μSEC FOR L-WAVE AND 3.30 MM/μSEC FOR S-WAVE. ERROR IN VELOCITY MEASUREMENT IS APPROXIMATELY ±0.1 PERCENT.

| Sample No. | Actual Damage+ (% Depth) | 0° L-Wave [FIG. 3(a)] | | Refracted Shear Wave [FIG. 3(c)] | | Refracted Creeping [FIG. 3(c)] | | [FIG. 3(e)] | |
|---|---|---|---|---|---|---|---|---|---|
| | | Min. Vel. | Δv % | Min. Vel. | Δv % | Min. Vel. | Δv % | Min. Vel. | Δv % |
| B-1  | 25++        | 5.90 | −0.6 | 5.79 | −2.5 | 3.28 | −0.6 |      |      |
| B-2  | 50          | 5.54 | −6.7 | 5.57 | −6.3 | 3.26 | −1.2 |      |      |
| B-3  | 50          | 5.61 | −5.5 | 5.39 | −9.3 | 3.16 | −4.3 | 5.90 | −0.7 |
| B-4  | 65          | 5.72 | −3.7 | 5.68 | −4.3 | 3.25 | −1.3 |      |      |
| B-5  | 65          | 5.57 | −6.2 | 5.41 | −8.9 | 3.24 | −1.8 | 5.89 | −0.9 |
| B-6  | 65          | 5.65 | −5.0 | 5.61 | −5.6 | 3.23 | −2.0 |      |      |
| B-7  | 50          | 5.50 | −7.3 | 5.55 | −6.5 | 3.24 | −1.7 | 5.72 | −3.7 |
| B-8  | 50          | 5.60 | −5.7 | 5.58 | −6.0 | 3.25 | −1.5 | 5.83 | −1.9 |
| B-9  | 65          | 5.59 | −5.8 | 5.51 | −7.2 | 3.23 | −2.0 | 5.82 | −2.0 |
| B-10 | 75          | 5.55 | −6.6 | 5.66 | −4.7 | 3.24 | −1.6 | 5.81 | −2.2 |
| B-11 | ID Scale    | 5.91 | −0.5 | 5.89 | −0.8 | 3.29 | −0.2 |      |      |
| B-12 | ID Pitting  | 5.91 | −0.5 | 5.88 | −1.0 | 3.29 | −0.2 |      |      |
| B-13 | ID Scale    | 5.91 | −0.5 | 5.94 | 0.0  | 3.28 | −0.4 |      |      |
| B-14 | Normal Tube | 5.93 | −0.3 |      |      |      |      | 5.90 | −0.6 |
| B-15 | Normal Tube | 5.95 | 0.1  | 5.90 | −0.6 | 3.27 | −0.8 | 5.93 | −0.2 |
| B-16 | Normal Tube | 5.93 | −0.2 | 5.89 | −0.8 | 3.28 | −0.6 | 5.93 | −0.1 |
| B-17 | Normal Tube | 5.93 | −0.1 | 5.89 | −0.8 | 3.28 | −0.5 | 5.94 | −0.1 |
| B-18 | ID Pitting  | 5.94 | 0.0  | 5.91 | −0.5 | 3.29 | −0.3 |      |      |
| B-19*| Normal Tube | 5.75 | 0.0  | 5.74 | −0.2 | 3.19 | −0.2 |      |      |

*Sample B-19 with machined pits had a lower nominal L-wave velocity of 5.75 mm/μsec and S-wave velocity of 3.20 mm/μsec.
+Damage measured on one end of the tube by etching.
++Damage localized in a small area towards one end of the tube.

The results in Table 1 also show that the amount of velocity reduction in a given specimen depends on the method used. This difference is expected for measurements taken in the axial and circumferential directions because of the difference in the damaged metal volume encountered by the wave. The axial measurement method averages the effect of hydrogen damage in the axial direction while the circumferential measurements average the velocities in the circumferential direction of the tube. For creeping waves, the depth of the creeping waves depends on the spacing between the transducers. Moreover, creeping-wave velocity measurements could not be taken on several samples, as shown in Table 2, as they were less than 63 mm (2.5 inches) long. This minimum length was found necessary for the creeping wave to penetrate in the metal volume affected by hydrogen.

From the velocity results, it is seen that the refracted L-wave, S-wave and the creeping-wave methods can be applied on boiler tubing. The former method is recommended because the signal is easier to interpret as L-wave velocity decreases more than S-wave velocity. The creeping-wave signal is usually very weak and requires a trained operator to identify this signal from other signals.

FIG. 6 illustrates another embodiment of the invention utilizing a single transducer 30 on the outer surface of a pipe 32 for detecting the presence of microcracks by a backscattering technique. However, this technique can be employed only in the absence of corrosion on the inner surface. Otherwise, backscattering from the corroded inner surface would obliterate the backscattered signal from the microcrack-damaged area. Backscattering increases with frequency so measurements are usually conducted at high frequencies between 10 and 20 MHz. Frequencies higher than 20 MHz suffer excessive attenuation of the backscattered signals for satisfactory results. Results of backscatter taken at 10 MHz show that backscatter amplitude (relative) increases by 16 to 21 dB on samples attacked by hydrogen compared to a sample with no hydrogen attack. The backscatter method has been applied to boiler tubes in the pulse echo mode in several configurations including normal incident L-waves and 75-degree refracted S-waves. The backscattering method is not found applicable on boiler tubes because the backscattering from hydrogen attack cannot be resolved from the scattering from the corroded inner surface. However, the backscatter method is applicable on piping systems in petrochemical plants where corrosion is not associated with hydrogen attack.

FIG. 7 is a block diagram of a field test system including a shoe 30 made from plexiglas for holding an ultrasonic transmitter 32 and an ultrasonic receiver 34. The shoe 30 is configured to mate with the outside surface of a boiler tube 36 with the transducers 32, 34 defining a fixed path for an ultrasonic wave 38 transmitted through the wall of tube 36. A conventional ultrasonic instrument 40 is connected to transmitter 32 and controls the transmission of ultrasonic signals. Electric signals from receiver 34 are connected to instrument 40. Instrument 40 is interconnected with conventional transit-time-measurement apparatus 42 to determine the transit time of the ultrasonic wave through the wall of tube 36.

Thus, the use of ultrasonic techniques in nondestructively testing for hydrogen attack based upon changes in velocity of ultrasonic waves in steel tubes and pipes has proved to be applicable in field applications. While the invention has been described with reference to specific embodiments, the description is illustrative of the invention and is not to be construed as limiting the invention. Various modifications and applications may occur to those skilled in the art without departing from the true spirit and scope of the invention as defined by the appended claims.

We claim:

1. A method of nondestructively testing for hydrogen attack in a steel body comprising the steps of
    (a) placing first and second ultrasound transducers on an outer surface of said body, said transducers being in fixed relationship to each other to define a fixed path length therebetween, (b) transmitting ultrasound waves from one of said transducers, (c) receiving said ultrasound waves by the other of said transducers, (d) determining velocities of the received waves with an accuracy of 0.1 percent of said ultrasound waves in said body from the fixed path length divided by time of travel of said ultrasound waves from said one transducer to said other transducer, a first of said received ultrasound waves being indicative of velocity through normal steel and a later of said received ultrasonic waves being indicative of hydrogen attack, and (e) determining the presence of hydrogen attack in the body from the difference in velocities of said received ultrasound waves through said body.

2. The method as defined by claim 1 wherein step (a) includes placing said transducers in a support shoe, said shoe establishing said fixed relationship, said shoe facilitating the testing of a steel body in the field.

3. The method as defined by claim 1 wherein said body comprises a steel pipe, and wherein step (b) includes transmitting longitudinal or shear waves in the chordal direction with the centerline of the beam tangential to the midthickness of the wall of said pipe.

4. The method as defined by claim 1 wherein step b) includes transmitting creeping waves (longitudinal waves refracted at 90 degrees).

5. The method as defined by claim 4 wherein aid creeping waves include a surface wave and a subsurface wave, and step d) includes determining the velocity difference between said surface wave and said subsurface wave.

6. Apparatus for nondestructively testing a steel body for hydrogen attack comprising first and second ultrasound transducers for transmitting and receiving ultrasound waves, a support structure for said two transducers for supporting said two transducers in fixed relationship to each other and thereby defining a fixed path length therebetween, said support means facilitating the testing of a steel body in the field, means for determining velocities of ultrasound waves transmitted through said body from the fixed path length divided by the time of travel of an ultrasound waves from one transducer to the other transducer, and means for determining the presence of hydrogen attack in said body from the velocity of said ultrasound waves transmitted through said body, a first of said ultrasound waves used to indicate velocity through normal steel and a later of said ultrasound waves used to indicate hydrogen attack.

7. Apparatus as defined by claim 6 wherein said support means includes a shoe for facilitating the testing of a steel body in the field.

8. Apparatus as defined by claim 7 wherein said shoe has a curved outer surface for mating with the outer surface of a tube undergoing test.

9. A method of nondestructively testing for hydrogen attack in a steel body comprising the steps of (a) placing a transducer on an outer surface of said body, (b) transmitting ultrasound waves from said transducer into said body, (c) receiving backscatter ultrasound waves from within said steel with said transducer, (d) measuring the amplitude of said backscatter ultrasound waves, and (e) determining the presence of hydrogen attack in the body from an increase in relative amplitude of said backscattered ultrasound waves.

* * * * *